(12) United States Patent
Guldbransen

(10) Patent No.: US 9,004,063 B1
(45) Date of Patent: Apr. 14, 2015

(54) PORTABLE OXYGEN INHALER DEVICE

(76) Inventor: Shane M. Guldbransen, Azle, TX (US)

(*) Notice: Subject to any disclaimer, the term of this patent is extended or adjusted under 35 U.S.C. 154(b) by 844 days.

(21) Appl. No.: 13/211,848

(22) Filed: Aug. 17, 2011

(51) Int. Cl.
A61M 11/00 (2006.01)
B65D 83/00 (2006.01)
B65D 88/54 (2006.01)
B67D 3/00 (2006.01)
A61M 11/04 (2006.01)

(52) U.S. Cl.
CPC .................................... A61M 11/04 (2013.01)

(58) Field of Classification Search
None
See application file for complete search history.

(56) References Cited

U.S. PATENT DOCUMENTS

| | | | |
|---|---|---|---|
| 2,896,825 A * | 7/1959 | Jackson | 222/211 |
| 3,278,086 A * | 10/1966 | Clouzeau et al. | 222/135 |
| 3,762,409 A * | 10/1973 | Lester | 128/200.14 |
| 4,093,124 A * | 6/1978 | Morane et al. | 239/327 |
| 4,671,270 A | 6/1987 | Kato | |
| 5,063,921 A * | 11/1991 | Howe | 128/200.14 |
| 5,224,472 A | 7/1993 | Pesenti et al. | |
| 5,544,647 A * | 8/1996 | Jewett et al. | 128/200.23 |
| 5,740,794 A * | 4/1998 | Smith et al. | 128/203.15 |
| 6,062,214 A * | 5/2000 | Howlett | 128/200.23 |
| 6,125,844 A | 10/2000 | Samiotes | |
| D433,502 S | 11/2000 | Rand | |
| 6,325,062 B1 * | 12/2001 | Sosiak | 128/203.25 |
| 6,390,090 B1 * | 5/2002 | Piper | 128/203.28 |
| 6,601,740 B1 * | 8/2003 | Clive | 222/484 |
| 7,051,731 B1 | 5/2006 | Rogerson | |
| 7,204,246 B1 | 4/2007 | Berinato | |
| 2003/0168526 A1 * | 9/2003 | Kienzler et al. | 239/533.2 |
| 2008/0097359 A1 * | 4/2008 | Hochrainer et al. | 604/295 |
| 2010/0199983 A1 * | 8/2010 | Jinks et al. | 128/200.23 |

* cited by examiner

Primary Examiner — Tan-Uyen T. Ho
Assistant Examiner — Eric Bryant

(57) ABSTRACT

An inhaler device having an air canister with a nozzle aperture and a nozzle shaft, the nozzle shaft has a first and second end, the first end is external to the canister and the second end protrudes into the canister, wherein a lip is at the second end, a gasket sandwiched between the nozzle aperture and shaft, a gasket extension extending downwardly, a spray orifice in the shaft at the first end, an external ventilation hole in the shaft external to the canister, an internal ventilation hole in the shaft, and an air channel in the nozzle shaft fluidly connected to each spray orifice, external and internal ventilation hole, wherein the nozzle shaft can move between an open and closed position, the nozzle shaft is biased in the closed position.

9 Claims, 3 Drawing Sheets (Cross-sectional Open View)

(ISO View)

(Front View)

(Top View)

(Cross-sectional Open View)

(Closed View)

(Alternative Embodiment)

PORTABLE OXYGEN INHALER DEVICE

FIELD OF THE INVENTION

The present invention is directed to an oxygen canister for oxygen or mixtures thereof, more particularly to an oxygen canister with additional holes to allow ambient air to mix with the oxygen prior to delivery.

BACKGROUND OF THE INVENTION

Medical professionals are typically the ones responsible for treating problems with shortness of breath and/or asthma, particularly in severe cases. The present invention features a novel portable oxygen inhaler device for delivering small amounts of oxygen. The device of the present invention can help individuals overcome bouts of shortness of breath (e.g., with or without the assistance of a medical professional). In some embodiments, the device of the present invention can also be used to help treat hangovers.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features an inhaler device. In some embodiments, the device comprises an air canister having a nozzle aperture; a nozzle shaft disposed in the nozzle aperture, the nozzle shaft has a first end and a second end, the first end is external to the canister and the second end protrudes into the canister, wherein a lip is disposed at or near the second end of the nozzle shaft; a gasket sandwiched between the nozzle aperture and the nozzle shaft; a gasket extension extending downwardly from the gasket in the direction of the second end of the nozzle shaft, the gasket extension snugly surrounds a portion of the nozzle shaft; a spray orifice disposed in the nozzle shaft at or near the first end of the nozzle shaft; an external ventilation hole disposed in the nozzle shaft external to the canister and positioned below the spray orifice; an internal ventilation hole disposed in the nozzle shaft inside the canister and positioned above the lip; and an air channel disposed in the nozzle shaft fluidly connected to each the spray orifice, the external ventilation hole, and the internal ventilation hole; wherein the nozzle shaft can move between at least an open position and a closed position, the nozzle shaft is biased in the closed position caused by a spring disposed in between the gasket and the lip, wherein in the closed position the tension of the spring draws the lip and gasket toward each other causing the gasket extension to cover the internal ventilation hole, wherein in the open position the nozzle shaft is moved farther into the canister so as to slide the internal ventilation hole away from the gasket extension allowing air from the canister to enter the air channel via the internal ventilation hole.

In some embodiments, the device comprises a mouthpiece component, the external ventilation hole being disposed in the mouthpiece component. In some embodiments, the spray orifice is between about $1/8$ to $1/16$ inches in diameter. In some embodiments, the spray orifice is between about $1/16$ to $1/32$ inches in diameter. In some embodiments, the spray orifice is between about $1/32$ to $1/64$ inches in diameter. In some embodiments, the ventilation holes are between about $1/8$ to $1/16$ inches in diameter. In some embodiments, the ventilation holes are between about $1/16$ to $1/32$ inches in diameter. In some embodiments, the ventilation holes are between about $1/32$ to $1/64$ inches in diameter. In some embodiments, the air channel extends from at or near the first end of the nozzle shaft to at or near the second end of the nozzle shaft.

DESCRIPTION OF PREFERRED EMBODIMENTS

Figure 1:
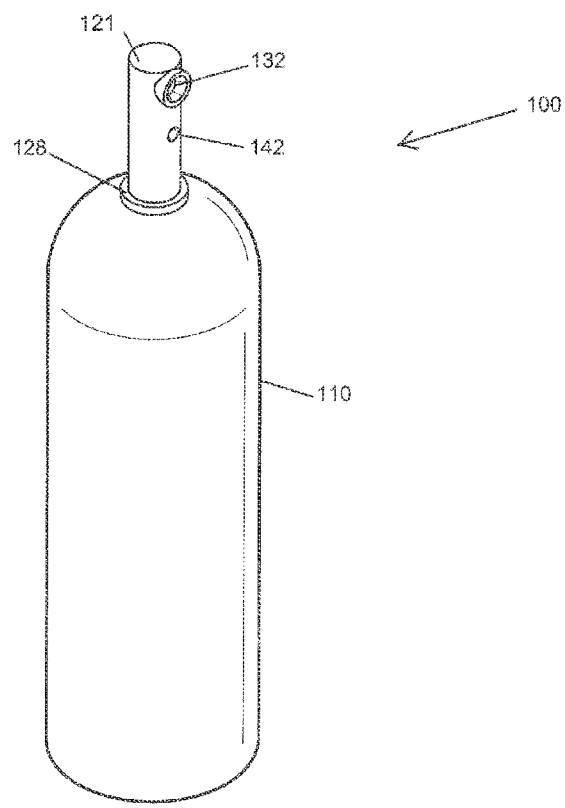
FIG. 1 is a perspective view of the portable oxygen inhaler device of the present invention.
Figure 2:
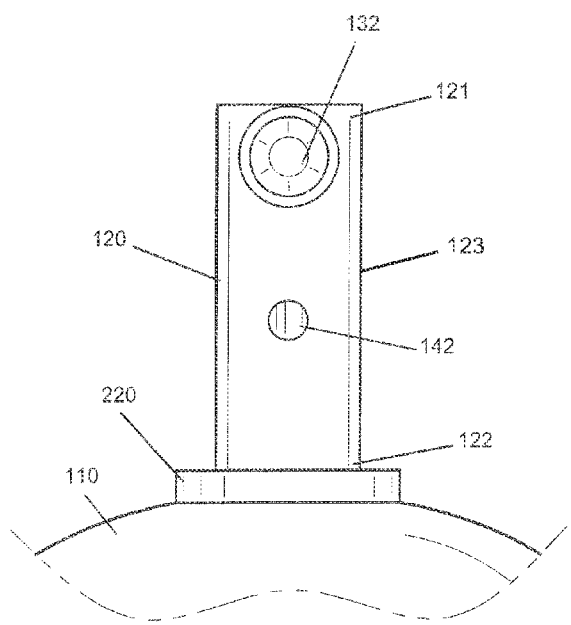
FIG. 2 is a front detailed view of the portable oxygen inhaler device of FIG. 1.
Figure 3:
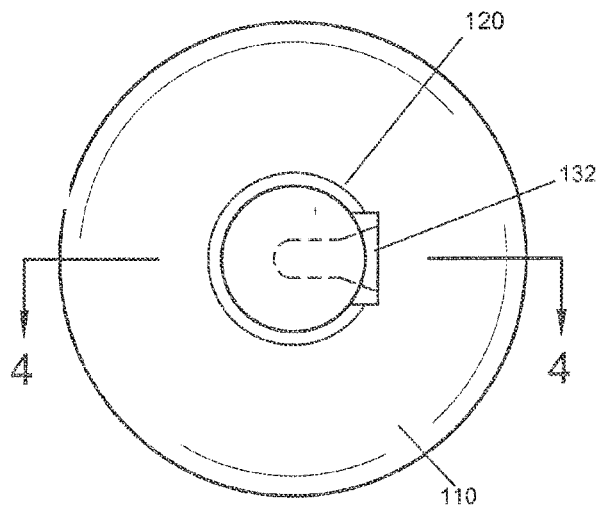
FIG. 3 is a top view of the portable oxygen inhaler device of FIG. 1.
Figure 4:
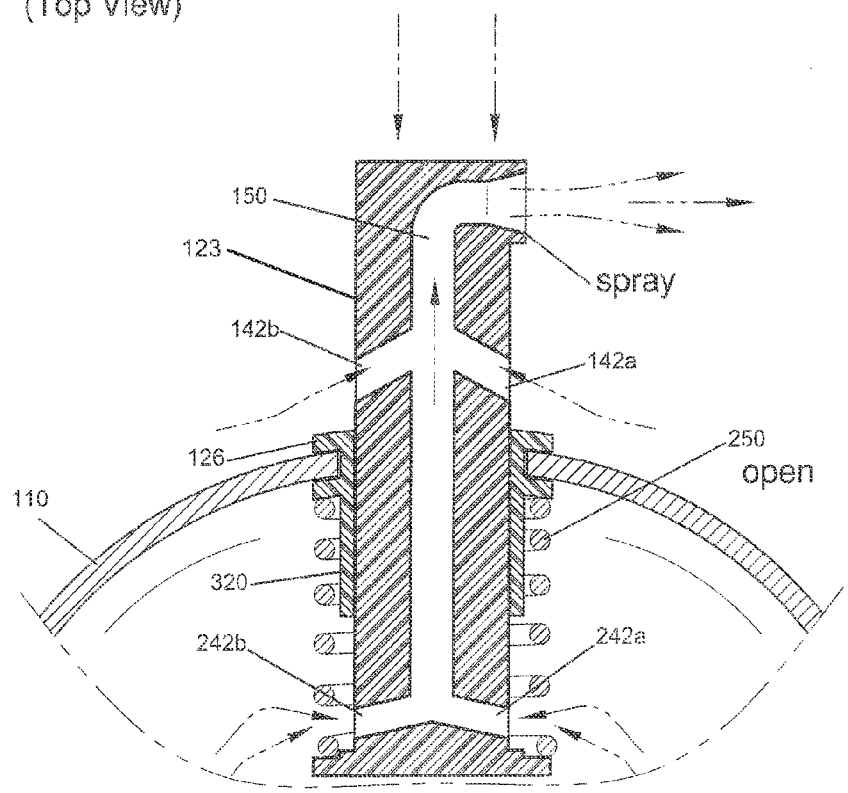
FIG. 4 is a side cross sectional view of the portable oxygen inhaler device of FIG. 3, wherein the nozzle shaft is in the open position.

Referring now to FIG. 1-6, the present invention features a novel portable oxygen inhaler device 100 for delivering small amounts of oxygen. The device 100 of the present invention comprises an air canister 110 for holding oxygen or a mixture thereof. Air canisters are well known to one of ordinary skill in the art.

Disposed in the top of the air canister 110 (e.g., is a nozzle aperture 128) is a nozzle shaft 120 having a first end 121 and a second end 122. In some embodiments, a gasket 126 is sandwiched between the nozzle aperture 128 and the nozzle shaft 120. The gasket 126 may help to prevent air from leaking out of the canister 110 (e.g., via the nozzle aperture 128). The second end 122 of the nozzle shaft 120 protrudes into the canister 110 (e.g., see FIG. 4, FIG. 5). A lip 220 is disposed at or near the second end 122 of the nozzle shaft 120. A gasket extension 320 extends downwardly from the gasket 122 (e.g., in the direction of the inside of the canister 110). The gasket extension 320 surrounds (e.g., snugly surrounds) a portion of the nozzle shaft 120 (e.g., see FIG. 4, FIG. 5).

A spray orifice 132 is disposed in the nozzle shaft 120, for example at or near the first end 121 of the nozzle shaft 120. One or more external ventilation holes 142 (e.g., a first external ventilation hole 142a, a second external ventilation hole 142b) are disposed in the nozzle shaft 120, e.g., above the canister 110, external to the canister 110, above the gasket 126, etc. The external ventilation holes 142 may be positioned below the spray orifice 132 (e.g., the spray orifice 132 is closer to the first end 121 of the nozzle shaft 120 than the ventilation holes 142). One or more internal ventilation holes 242 (e.g., a first internal ventilation hole 242a, a second internal ventilation hole 242b) are disposed in the nozzle shaft 120, e.g., inside the canister 110, below the gasket 126, etc. The internal ventilation holes 242 are positioned above the lip 220 (e.g., see FIG. 4).

An air channel 150 is disposed in the nozzle shaft 120. The air channel 150 extends from at or near the first end 121 of the nozzle shaft 120 to at or near the second end 122 of the nozzle shaft 120. The air channel 150 is fluidly connected to the spray orifice 132, the external ventilation holes 142, and the internal ventilation holes 242.

Figure 5:
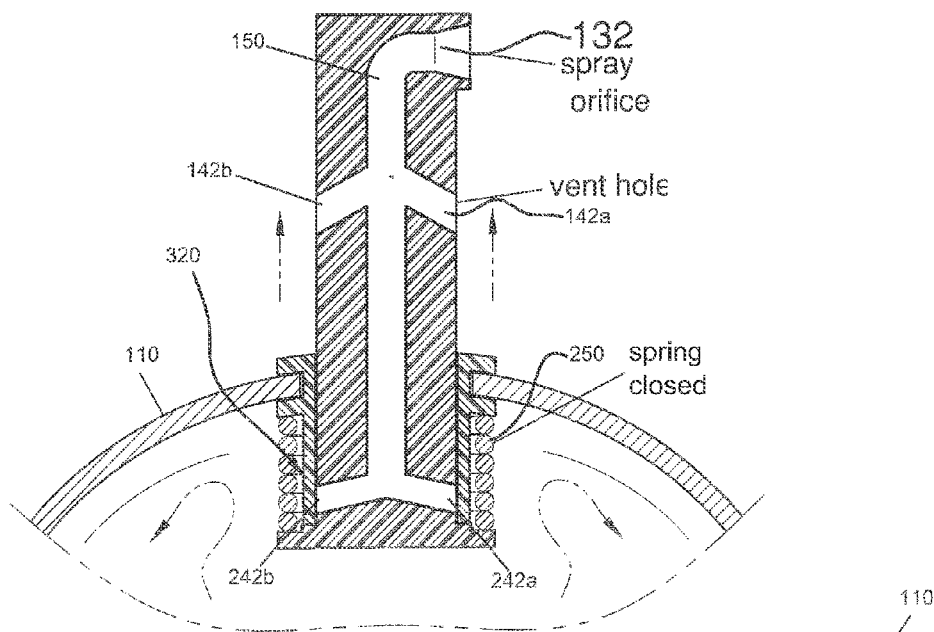
FIG. 5 is a cross sectional view of the portable oxygen inhaler device, wherein the nozzle shaft is in the closed position.
Figure 6:
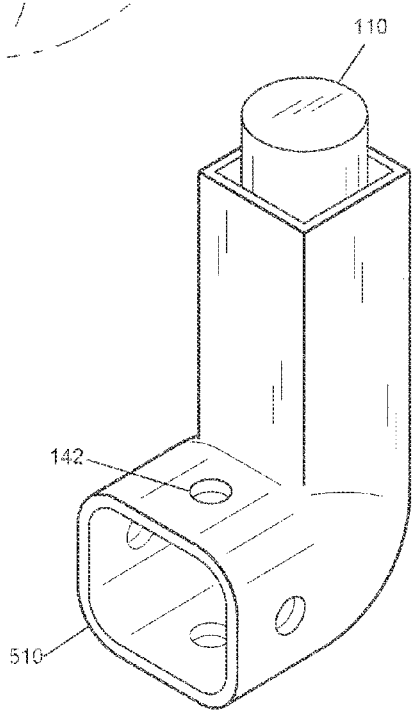
FIG. 6 is an alternative embodiment of the portable oxygen inhaler device of the present invention.

The nozzle shaft 120 can move between multiple positions including but not limited to an open position (see FIG. 4) and a closed position (see FIG. 5). The nozzle shaft 120 is biased in the closed position caused by a spring 250 (e.g., tension spring) disposed in between the gasket 126 and the lip 220 (e.g., attached to the gasket 126 and the lip 220). The tension of the spring 250 draws the lip 220 upwardly (e.g., toward the gasket 126), causing the internal ventilation holes 242 to be covered by the gasket extension 320. The gasket extension 320 prevents air from the canister 110 from entering the internal ventilation holes 242. In some embodiments, in the closed position, the gasket extension 320 contacts the lip 220. To move the nozzle shaft 120 to the open position, the nozzle shaft 120 is pressed into the canister 110 (e.g., pressed a certain distance into the canister 110). Moving the nozzle shaft 120 in this manner slides the internal ventilation holes 242 away from the gasket extension 320, allowing air from the canister 110 to enter the air channel 150 via the internal ventilation holes 242. Ambient air can enter the air channel 150 via the external ventilation holes 142 (the ambient air can mix with the canister air in the air channel 150). The mixture of air can exit the air channel 150 via the spray orifice 312. A user can inhale the air from the spray orifice 312. When the nozzle shaft 120 is released, the spring 250 causes the nozzle shaft 120 to return to the closed position.

The device 100 of the present invention may be constructed in an inhaler form. Inhalers are well known to one of ordinary skill in the art. For example, the device 100 may comprise a generally L-shaped mouthpiece component 510 that stores the canister 110 and provides an end for inserting into a user's mouth (see FIG. 6). The external ventilation holes 142 are disposed in the mouthpiece component 510.

The device 100 of the present invention may be constructed in a variety of sizes. For example, in some embodiments, the spray orifice 132 and/or the ventilation holes 142, 242 are between about 1/8 to 1/16 inches in diameter. In some embodiments, the spray orifice 132 and/or the ventilation holes 142, 242 are between about 1/16 to 1/32 inches in diameter. In some embodiments, the spray orifice 132 and/or the ventilation holes 142, 242 are between about 1/32 to 1/64 inches in diameter. The present invention is not limited to the aforementioned dimensions.

As used herein, the term "about" refers to plus or minus 10% of the referenced number. For example, an embodiment wherein the ventilation holes 142, 242 are about 1/8 inch (0.125 inches) include ventilation holes 142, 242 that are between 0.1125 and 0.1375 inches in diameter.

The disclosures of the following U.S. Patents are incorporated in their entirety by reference herein: U.S. Pat. No. 7,204,246; U.S. Pat. No. 4,671,270; U.S. Pat. No. 6,125,844; U.S. Pat. No. 7,051,731; U.S. Pat. No. 5,224,472; U.S. Design Pat. No. D433,502.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. An inhaler device (100) comprising:
   (a) a canister (100) having a nozzle aperture (128);
   (b) a nozzle shaft (120) disposed in the nozzle aperture (128), the nozzle shaft (120) has a first end (121) and a second end (122) and an outer side (123), the first end (121) is external to the canister (110) and the second end (122) protrudes into the canister (110), wherein a lip (220) is disposed at the second end (122) of the nozzle shaft (120); wherein the outer side (123) is between the first end (121) and the second end (122);
   (c) a gasket (126) sandwiched between the nozzle aperture (128) and the nozzle shaft (120);
   (d) a gasket extension (320) extending downwardly from the gasket (126) in a direction of the second end (122) of the nozzle shaft (120), the gasket extension (320) surrounds a portion of the nozzle shaft (120);
   (e) a spray orifice (132) disposed in the nozzle shaft (120) at or near the first end (121) of the nozzle shaft (120);
   (f) an external ventilation hole (142) disposed in the nozzle shaft (120) external to the canister (110) and positioned below the spray orifice (132), wherein the external ventilation hole (142) is disposed in the outer side (123) of the nozzle shaft (120);
   (g) an internal ventilation hole (242) disposed in the nozzle shaft (120) inside the canister (110) and positioned above the lip (220); and
   (h) an air channel (150) disposed in the nozzle shaft (120) fluidly connected to each the spray orifice (132), the external ventilation hole (142), and the internal ventilation hole (242);
   wherein the nozzle shaft (120) can move between at least an open position and a closed position, the nozzle shaft (120) is biased in the closed position caused by a spring (250) disposed in between the gasket (126) and the lip (220), wherein in the closed position a tension of the spring (250) draws the lip (220) and gasket (126) toward each other causing the gasket extension (320) to cover the internal ventilation hole (242), wherein in the open position the nozzle shaft (120) is moved farther into the canister (110) so as to slide the internal ventilation hole (242) away from the gasket extension (320) allowing air from the canister (110) to enter the air channel (150) via the internal ventilation hole (242);
   whereupon in the open position, air passes through the external ventilation hole (242) and into the air channel (150).

2. The device (100) of claim 1, wherein the spray orifice (132) is between about 1/8 to 1/16 inches in diameter.

3. The device (100) of claim 1, wherein the spray orifice (132) is between about 1/16 to 1/32 inches in diameter.

4. The device (100) of claim 1, wherein the spray orifice (132) is between about 1/32 to 1/64 inches in diameter.

5. The device (100) of claim 1, wherein the internal ventilation hole (142) and external ventilation hole (242) are between about 1/8 to 1/16 inches in diameter.

6. The device (100) of claim 1, wherein the internal ventilation hole (142) and external ventilation hole (242) are between about 1/16 to 1/32 inches in diameter.

7. The device (100) of claim 1, wherein the internal ventilation hole (142) and external ventilation hole (242) are between about 1/32 to 1/64 inches in diameter.

8. The device (100) of claim 1, wherein the air channel (150) extends from at or near the first end (121) of the nozzle shaft (120) to at the second end (122) of the nozzle shaft (120).

9. An inhaler device (100) consisting of:
   (a) a canister (110) having a nozzle aperture (128);
   (b) a nozzle shaft (120) disposed in the nozzle aperture (128), the nozzle shaft (120) has a first end (121) and a second end (122) and an outer side (123), the first end (121) is external to the canister (110) and the second end (122) protrudes into the canister (110), wherein a lip (220) is disposed at the second end (122) of the nozzle shaft (120); wherein the outer side (123) is between the first end (121) and the second end (122);
   (c) a gasket (126) sandwiched between the nozzle aperture (128) and the nozzle shaft (120);
   (d) a gasket extension (320) extending downwardly from the gasket (126) in a direction of the second end (122) of the nozzle shaft (120), the gasket extension (320) surrounds a portion of the nozzle shaft (120);
   (e) a spray orifice (132) disposed in the nozzle shaft (120) at or near the first end (121) of the nozzle shaft (120);
   (f) an external ventilation hole (142) disposed in the nozzle shaft (120) external to the canister (110) and positioned below the spray orifice (132), wherein the external ventilation hole (142) is disposed in the outer side (123) of the nozzle shaft (120);
   (g) an internal ventilation hole (242) disposed in the nozzle shaft (120) inside the canister (110) and positioned above the lip (220); and
   (h) an air channel (150) disposed in the nozzle shaft (120) fluidly connected to each the spray orifice (132), the external ventilation hole (142), and the internal ventilation hole (242);
   wherein the nozzle shaft (120) can move between at least an open position and a closed position, the nozzle shaft (120) is biased in the closed position caused by a spring (250) disposed in between the gasket (126) and the lip (220), wherein in the closed position a tension of the spring (250) draws the lip (220) and gasket (126) toward each other causing the gasket extension (320) to cover the internal ventilation hole (242), wherein in the open position the nozzle shaft (120) is moved farther into the canister (110) so as to slide the internal ventilation hole (242) away from the gasket extension (320) allowing air from the canister (110) to enter the air channel (150) via the internal ventilation hole (242);
   whereupon in the open position, air passes through the external ventilation hole (242) and into the air channel (150).

\* \* \* \* \*